United States Patent [19]  
Pakulis

[11] Patent Number: 4,767,981  
[45] Date of Patent: Aug. 30, 1988

[54] MOISTURE CONTENT DETECTOR

[75] Inventor: Ivars E. Pakulis, Elgin, Ill.

[73] Assignee: Advanced Moisture Technology, Inc., Buffalo Grove, Ill.

[21] Appl. No.: 869,303

[22] Filed: Jun. 2, 1986

[51] Int. Cl.⁴ .............................................. G01R 2704
[52] U.S. Cl. ........................... 324/58.5 A; 324/58.5 R
[58] Field of Search ................... 324/58.5 R, 58.5 M, 324/58.5 B, 58.5 C

[56] References Cited

U.S. PATENT DOCUMENTS

| | | | |
|---|---|---|---|
| 2,659,860 | 11/1953 | Breazeale | 324/49 |
| 3,290,598 | 12/1966 | Thomas | 325/67 |
| 3,295,133 | 12/1966 | Emerson et al. | 343/18 |
| 3,460,030 | 8/1969 | Brunton et al. | 324/58.5 |
| 3,499,499 | 3/1970 | Bilbrough . | |
| 3,501,692 | 3/1970 | Kluck | 324/58.5 |
| 3,534,260 | 10/1970 | Walker | 324/58.5 |
| 3,553,573 | 1/1971 | Lundstrom et al. | 324/58.5 |
| 3,681,684 | 8/1972 | Busker et al. | 324/58.5 A |
| 3,693,079 | 9/1972 | Walker | 324/58.5 A |
| 3,815,019 | 6/1974 | Wiles | 324/58.5 A |
| 3,818,333 | 6/1974 | Walker | 324/58.5 A |
| 4,103,224 | 7/1978 | Taro et al. | 324/58.5 C |
| 4,104,584 | 8/1978 | Miyai et al. | 324/58.5 R |
| 4,131,845 | 12/1978 | Pakulis | 324/58.5 A |
| 4,206,399 | 6/1980 | Fitzky et al. | 324/58.5 C |
| 4,514,680 | 4/1985 | Heikkilä et al. | 324/58.5 R |
| 4,546,311 | 10/1985 | Köchel | 324/58.5 R |
| 4,620,146 | 10/1986 | Ishikawa et al. | 324/58.5 A |

FOREIGN PATENT DOCUMENTS 0951130  8/1982  U.S.S.R. .......................... 324/58.5 R

OTHER PUBLICATIONS

5th European Microwave Conference (Hamburg, Germany), pp. 223–227, Sep. 1975, "A Microwave Attenuation Comparator as an Industrial On-Line Moisture Controller", Jerzy Kolinski.
IEEE Transaction on Industrial Electronics and Control Instrumentation, vol. IECI-23, No. 4, pp. 364–370, Nov. 1976, published by Institute of Electrical and Electronic Engineers, N.Y., N.Y., Title: An Improved Microwave Method of Moisture Content Measurement and Control, Authors: A. Kraszewski and S. Kulinski.

Primary Examiner—Philip H. Leung
Assistant Examiner—Jeffrey A. Gaffin
Attorney, Agent, or Firm—Wood, Dalton, Phillips, Mason & Rowe

[57] ABSTRACT

An improved moisture detection apparatus for use in detecting moisture in discrete objects brought seriatim to a sensing zone. The apparatus includes structure for transmitting a beam of microwave energy having a planar wavefront through a portion of the object brought to the sensing zone and utilizing signal processing structure for selectively providing peak detection or averaging integration of the microwave beam signal in providing desired accuracy in the determination of the moisture content of such objects which may vary in uniformity of the moisture content thereof. Microwave absorber material is provided in the signal path between the microwave horns and the object. The invention includes structure for accurately aligning the horns notwithstanding the use of an opaque conveyor for bringing the objects to the sensing zone interposed between the horns.

13 Claims, 1 Drawing Sheet

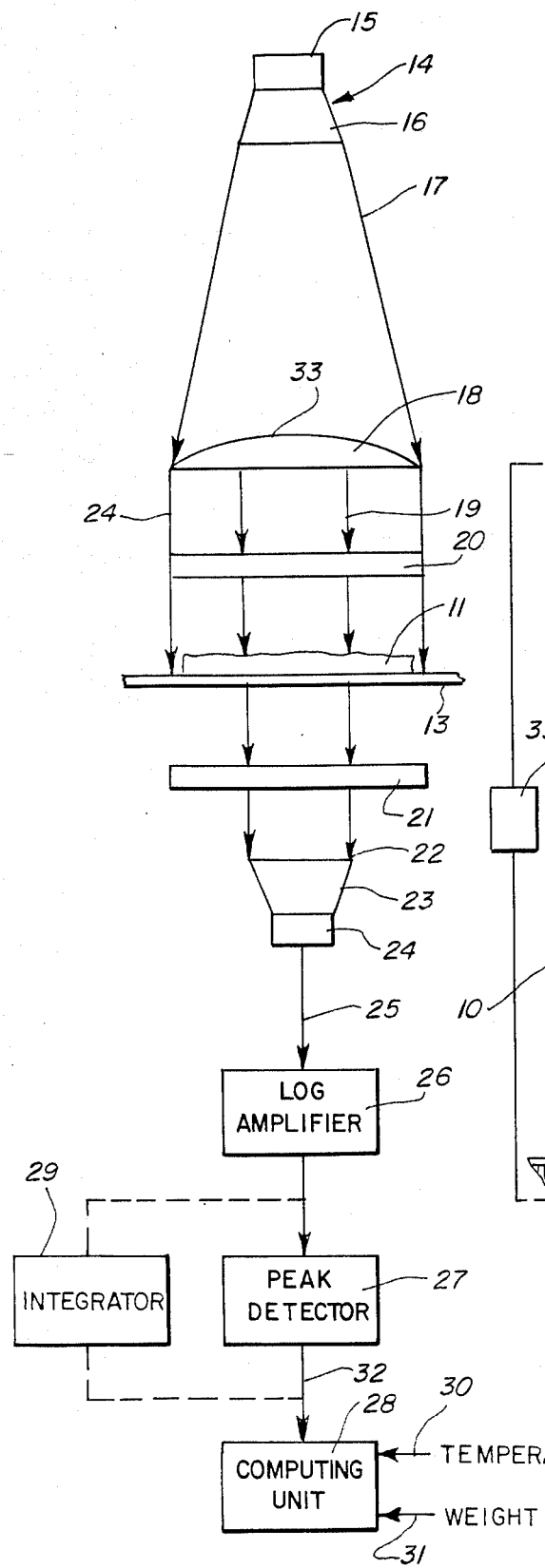
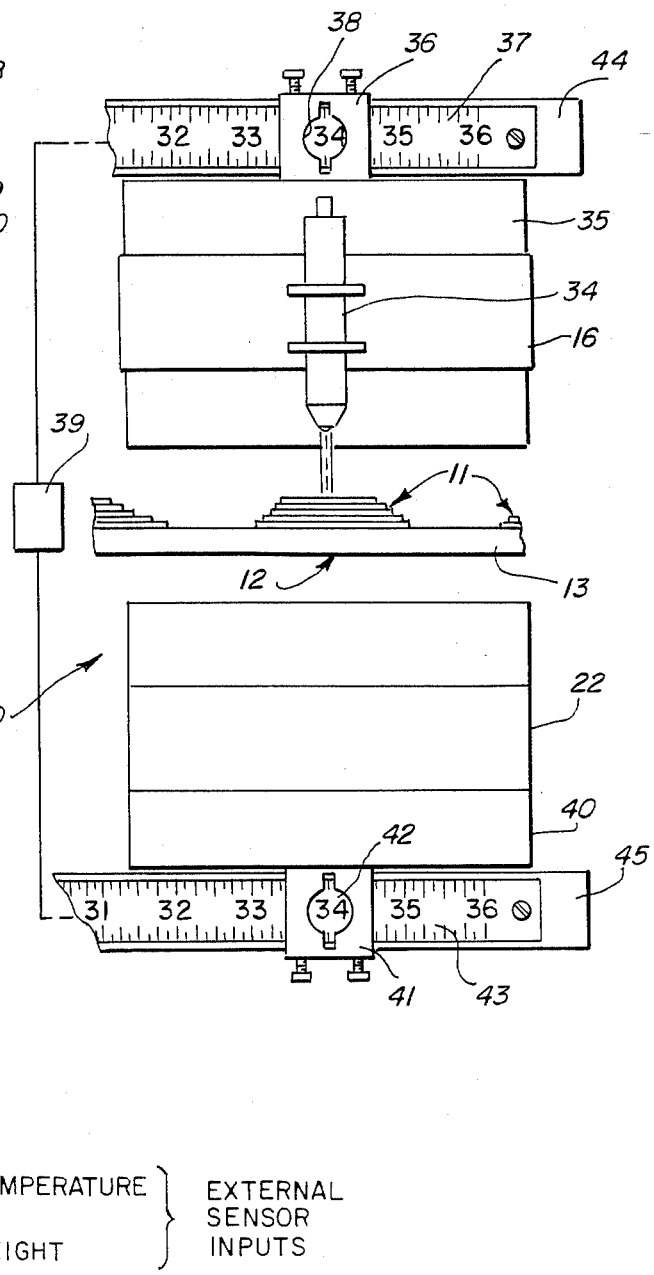

MOISTURE CONTENT DETECTOR

TECHNICAL FIELD

This invention relates to moisture content detectors and in particular to apparatus for detecting the moisture content seriatim in a plurality of objects.

BACKGROUND ART

It has been conventional to determine the moisture content of objects for material samples by placement thereof in a well through which is passed microwave energy from a transmitting horn antenna to a receiving horn antenna. An excellent example of such a moisture detection apparatus is disclosed in U.S. Pat. No. 4,716,360 issued Dec. 29, 1987, entitled "Moisture Detector Apparatus and Method". As disclosed in said application, lenses may be associated with the transmitting and receiving antennas for providing improved transmission of the microwave energy through the sample.

It is further conventional to detect moisture content in bulk material as it is conducted through a sensing zone as by means of a conveyor belt or conveyor trough. One example of such an apparatus is disclosed in U.S. Pat. No. 3,460,030 of Donald C. Brunton et al.

DISCLOSURE OF INVENTION

The present invention comprehends an improved moisture content detector for use in detecting the moisture content seriatim of a plurality of objects passed transversely through a beam of microwave radiation. The beam cross section is preselected to be of lesser extent than the transverse extent of the object.

In the illustrated embodiment, the receiving means has a transverse section smaller than the smallest transverse section of the object.

The invention comprehends providing the radiation in the form of a tightly collimated beam.

The invention further comprehends the provision of improved means for centering the receiving means relative to the beam passed through the objects.

In the illustrated embodiment, the means for determining the attenuation of the beam comprises means for determining the maximum attenuation caused individually by a preselected plurality of the objects.

Thus, the invention is adapted for use with a system wherein conveying means provides the objects seriatim in association with the sensing beam.

The invention comprehends that the conveyor may be opaque to light and the means for locating the receiving means is adapted to provide accurate alignment of the receiving means with the transmitting means, notwithstanding the opaqueness of the conveyor means.

Means are provided adjacent the receiving means for absorbing microwave energy of the transmitted beam laterally of the preselected portion thereof detected by the receiving means.

In the illustrated embodiment, the received beam portion has a maximum transverse extent of less than approximately 2".

The moisture sensing apparatus of the present invention is extremely simple and economical of construction while yet providing for highly improved sensing of the moisture content of discrete objects in a continuous manner.

BRIEF DESCRIPTION OF THE DRAWING

Other features and advantages of the invention will be apparent from the following description taken in connection with the accompanying drawing wherein:

FIG. 1 is a diagrammatic elevation of an apparatus embodying the invention; and

FIG. 2 is a fragmentary elevation of the apparatus.

BEST MODE FOR CARRYING OUT THE INVENTION

In the illustrative embodiment of the invention as disclosed in the drawing, apparatus generally designated 10 is provided for detecting the moisture content of objects, such as illustrative objects 11, brought seriatim to a sensing position generally designated 12 by a conveyor 13. As indicated above, the present invention is concerned with the problems arising in the attempted sensing of the moisture content of discrete objects as distinguished from the continuous measurement of materials, such as in continuous web sensing processes or in connection with the translation of bulk materials on a conveyor.

More specifically, the discontinuities and irregularities associated with discrete objects translated in a single layer on a process line have prevented the satisfactory use of the presently available moisture analyzers. Thus, it has been found that the present moisture analyzers are incapable of providing the necessary accuracy suitable for desired process control purposes and the like. One attempted solution to the problem has been to use off-line discrete sample analyzers and such analyzers, while having high accuracy, are unsatisfactory in not being able to continuously monitor the moisture content of all of the objects at a relatively high speed.

In the illustrated embodiment, the objects 11 comprise bakery products, it being understood that the invention is adapted for use with any type of object requiring moisture level determination, such as in a processing line.

Conventionally, bakery goods, such as cookies, buns etc., are formed and shaped upstream of an oven, or drier, through which they are subsequently conveyed, to emerge from the heating process in one or more rows. It has been found to be highly important to maintain desired moisture content in the products and, as discussed above, it has been found impractical in the past to obtain continuous process moisture measurement in such applications.

A number of factors have aggravated the problem, including variations in the spacing between the objects on the conveyor, the nonsymmetrical or nonuniform geometry of the items, and the fact that the moisture content varies from edge to edge or from top to bottom of the objects.

It has been found desirable in certain applications to determine the moisture profile of the object, as well as to obtain average moistures of a number of the objects as they pass through the moisture sensing means. As indicated in the prior art as discussed above, microwave energy is useful in determining the moisture content by virtue of its ability to penetrate into the object and measure the moisture within as well as the outer surfaces thereof.

The present invention comprehends the provision of an improved apparatus 10 for providing highly accurate moisture determinations of a plurality of objects brought seriatim to the sensing zone at relatively high speed.

More specifically, the invention comprehends the provision of such an apparatus wherein a source, generally designated 14, of microwave energy comprises a generator 15 and a radiating horn 16. A beam, generally designated 17, of microwave energy is passed through a collimating lens 18 and the collimated beam is passed through a layer of microwave absorbing material 20 and thence through the object 11 carried on the conveyor 13.

As shown in FIG. 1, the transverse extent of the object is preferably greater than the transverse extent of the microwave receiving means and, thus, the moisture content of only a portion of the object is instantaneously determined as the object is moved through the beam portion 19 on the conveyor. The beam portion 19 corresponds with the transverse extent of the receiving means.

The microwave energy passes through the object portion and conveyor and thence through a second microwave energy absorbing material 21 to the input 22 of a receiving horn 23 which, as shown, has a transverse extent substantially less than the maximum transverse extent of the collimated beam 24 emerging from the collimating lens 18. As shown, the transverse extent of the horn is that of the collimated beam portion 19.

The received microwave energy is detected by a suitable detector 24, with the signal 25 being fed through a log amplifier 26 and peak detector 27 to a conventional computing unit 28.

A conventional integrator 29 may be utilized in lieu of the peak detector, in some applications.

Both a temperature signal 30 and a weight signal 31 may be provided to the computing unit as external inputs in the normal manner so as to provide the necessary information in coordination with the moisture detecting input signal 32 delivered to the computer from the peak detector or integrator, as desired.

Horn antenna 16 preferably has a relatively large aperture so as to produce a more tightly collimated beam. In the illustrated embodiment, the transmitting horn 16 produces a beam width of 35° or less.

The divergent beam 17 is caused to define a parallel plane wavefront beam by means of the lens 18. In the illustrated embodiment, the planoconvex refracting lens has a hyperbolic curved surface 33 facing the transmitting horn 16.

In order to avoid resonances and reflections between the transmitting horn 16 and the objects 11, the layer of microwave absorbing material is interposed in the beam transmitted through the lens 18. Beam portion 19 corresponds to the entrance 22 of the receiving horn 23 and, thus, all of the collimated radiation received by the receiving horn passes through the microwave absorbing means 20.

A second layer of microwave absorbing material 21 is interposed between the conveyor 13 and the entrance 22 to the receiving horn, as shown in FIG. 1, to provide further reduction in resonances and reflections in the sensing of the moisture content of the objects 11.

As a wide swing in the signal received by the receiving horn 23 and detector 24 occurs because of the provision of the discrete objects in spaced relationship on conveyor 13, it is desirable to use a log amplifier 26. As will be obvious to those skilled in the art, the handling of the output of the log amplifier may be effected by means of two different forms of signal handling apparatus, including a conventional peak detector 27 or a conventional integrator 29. The use of the integrator for providing an averaging output signal 32 is adequate where production rates are constant and the product reasonably uniform. Where such uniformity is not expected, it is preferable to utilize the peak detector apparatus 27 in providing the signal 32 to the computing unit 28.

As indicated in FIG. 1, it is desirable to provide inputs to the computing unit, such as the product weight and the product temperature, for improved accuracy by providing suitable compensation in the computing unit, as will be obvious to those skilled in the art.

It has been found that in many objects, such as cookies, the moisture varies from the outer edges to the center thereof. In order to provide an accurate and correct reading of the moisture in such objects, it is desirable to accurately align the microwave beam with the center of the object. To assure such accuracy in the use of the apparatus, an optical light source 34 is mounted at the center of the transmitting horn 16 and the assembly thereof mounted to a suitable fixture 35 having a slide 36 slidably carried on a linear scale element 37. An aperture 38 in the slide provides an accurate reading of the location of the center of the optical light source relative to a mounting base structure 39 shown diagrammatically in FIG. 2.

The receiving horn 22 is centered relative to the light source by locating its center in direct correspondence with the location of the center of the light source 34 determined by the reading seen through the aperture 38 in the slide 36. For this purpose, the horn 22 is mounted to a fixture 40 provided with a slide 41 having an aperture 42 for reading the location of the scale 43 on which the slide is mounted. Thus, by aligning the aperture 42 with the same scale reading as observed through the aperture 38 of slide 36, accurate centering of the receiving horn relative to the transmitting horn is effected notwithstanding the use of an optically opaque conveying belt 13, as illustrated in FIG. 2.

Thus, the invention comprehends the use of asymmetrical horn apertures in a novel manner so as to provide an improved accurate moisture detection system. In the illustrated embodiment, the receiving horn is caused to have a substantially smaller aperture than that of the transmitting horn. The invention comprehends converting the divergent conical beam 17 of the transmitting horn to one having a planar wavefront by means of the lens 18 and the utilization of microwave absorbing material 20 in the signal path between the microwave horns and the object, the moisture of which is being measured.

The invention further comprehends the provision of means for assuring accurate centering of the receiving horn notwithstanding the use of a visually opaque conveyor belt on which the objects are seriatim brought to the sensing zone.

The invention comprehends the use of peak detection in the signal processing for determination of moisture in products where nonuniform distribution of the moisture occurs in the objects. Alternatively, the invention comprehends the use of an integrator in the signal processing system when substantially uniform moisture characteristics are anticipated.

In the illustrated embodiment, the horns are supported on arms 44 and 45, respectively, carrying the scale means 37 and 43, respectively. Thus, the arms may comprise relatively long cantilevered supports providing desirable rigidity and maintained accuracy in the positioning of the horns.

Thus, the invention comprehends an improved moisture detector permitting the detection of moisture in discrete objects brought seriatim to a detection zone on conveyor means, permitting the spacing of the objects one from the other as in conventional mass production systems.

The collimated beam utilized to sense the moisture is preferably substantially smaller in transverse cross section than the object so that different portions of the object may be selectively utilized in the sensing operation. Means are provided for utilizing the information determined by the relatively small cross section sensing beam for providing desired accuracy in the indication of the moisture content of the object under different conditions of uniformity of the moisture therein.

The foregoing disclosure of specific embodiments is illustrative of the broad inventive concepts comprehended by the invention.

I claim:

1. A moisture content detector comprising:
    generating means for generating and transmitting a beam of microwave radiation having a first preselected cross-sectional area;
    means for collimating said beam;
    receiving means for receiving only a preselected portion of said beam having a second preselected cross-sectional area less than said first crosssectional area;
    conveying means for disposing objects seriatim in said beam between said generating means and said receiving means, said beam portion being preselected to be of lesser cross-sectional area of the individual objects to be disposed in said beam portion; and
    attenuation determining means for determining an attenuation of said beam portion caused by the objects corresponding to the moisture content thereof.

2. The moisture content detector of claim 1 further including means for centering said receiving means relative to said object.

3. The moisture content detector of claim 1 wherein said means for determining the attenuation of said beam comprises means for determining the maximum attenuation caused individually by a preselected plurality of the objects.

4. The moisture content detector of claim 1 wherein said conveying means comprises a continuously moving conveying means.

5. The moisture content detector of claim 1 wherein said conveying means comprises a continuously moving opaque conveying means.

6. The moisture content detector of claim 1 wherein said conveying means comprises a continuously moving opaque conveying means and further including means for centering said receiving means relative to said object comprising means for accurately locating said receiving means relative to said generating means, and means for centering said object relative to said generating means in determining said attenuation by said determining means.

7. The moisture content detector of claim 1 further including means adjacent said receiving means for absorbing the microwave energy of the transmitted beam laterally of said preselected beam portion.

8. The moisture content detector of claim 1 wherein said preselected beam portion has a maximum transverse extent of less than approximately 2 inches.

9. The moisture content detector of claim 1 further including means for centeriing said receiving means relative to said beam portion and said means for determining the attenuating of said beam comprises means for determining the maximum attenuation caused individually by a preselected plurality of the objects successively centered relative to said beam portion.

10. A moisture content detector comprising:
    generating means for generating and transmitting a beam of microwave radiation having a first preselected cross-sectional area;
    means for collimating said beam;
    receiving means for receiving a preselected minor portion only of said beam having a second preselected cross-sectional area less than said first cross-sectional area;
    conveying means for disposing objects seriatim in said beam between said generating means and said receiving means, said beam portion being preselected to be of lesser cross-sectional area than the cross-sectional area of the individual objects to be disposed in said beam portion; and
    attenuation determining means for determining an attenuation of said beam portion caused by the objects corresponding to the moisture content thereof.

11. The moisture content detector of claim 10 wherein said preselected beam portion has a maximum transverse extent of less than approximately 2 inches.

12. The moisture content detector of claim 10 further including means for centering said receiving means relative to said object.

13. The moisture content detector of claim 10 wherein said means for determining the attenuation of said beam comprises means for determining the maximum attenuation caused individually by a preselected plurality of the objects.

* * * * *